Figure 1:
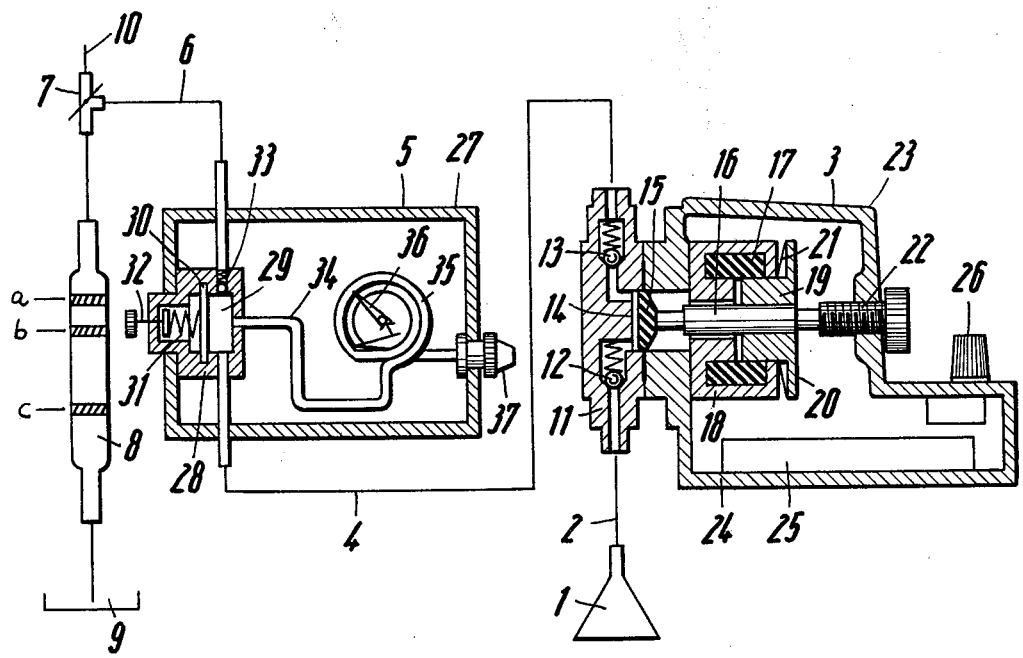

United States Patent [19]
Ernst et al.

[11] 3,984,315
[45] Oct. 5, 1976

[54] ELECTROMAGNETIC METERING PUMP

[75] Inventors: Franz Ernst, Heidelberg; Viktor Dulger, Heidelberg-Kirchberg, both of Germany

[73] Assignee: Chemie und Filter GmbH Verfahrenstechnik KG, Heidelberg, Germany

[22] Filed: Apr. 3, 1975

[21] Appl. No.: 564,796

[30] Foreign Application Priority Data

Apr. 26, 1974  Germany............................ 2420180

[52] U.S. Cl. .......................... 210/31 C; 210/198 C; 210/349
[51] Int. Cl.[2] ........................................ B01D 15/08
[58] Field of Search ............ 210/31 C, 24 C, 198 C, 210/349

[56] References Cited
UNITED STATES PATENTS

| | | |
|---|---|---|
| 3,493,496 | 2/1970 | Bray et al. ....................... 210/349 X |
| 3,537,585 | 11/1970 | Waters ............................ 210/349 X |
| 3,855,129 | 12/1974 | Abrahams ....................... 210/198 C |

*Primary Examiner*—John Adee

[57] ABSTRACT

Apparatus for pumping the eluent liquid through a chromatograph column is provided in the form of an electromagnetic metering pump, the outlet of which is provided with a pulsation damping device in the form of a sealed chamber having a resiliently loaded elastic wall. Considerable control of operation is obtainable by adjustment of the resilient loading and the operation of the pump (speed and stroke length). The chamber may be fitted with a pressure gauge having a closable outlet to atmosphere for purging purposes. Effective chromatographic separation of mixtures is obtainable at low equipment costs.

11 Claims, 2 Drawing Figures

U.S. Patent   Oct. 5, 1976   3,984,315

ELECTROMAGNETIC METERING PUMP

The present invention relates to apparatus for use in liquid chromatography and has as an object the provision of improved pumping apparatus for passing the liquid through a chromatographic column containing an adsorption agent.

In liquid chromatography, the liquid is usually passed through the column continuously at a low rate of flow. In low pressure chromatography the very low constant rate of flow is obtained by a simple hydrostatic arrangement in which the liquid is supplied from a header tank. In high pressure chromatography a pump is used to force the liquid through the column at the desired pressure, for example from 100 to 200 atmospheres. For example, a pump is used which has a piston which is moved gradually by a cam in the forward direction and quickly returned. In order to alter the speed of operation a control device must be provided between the motor and the cam. Because of their complex construction pumps of this type are expensive.

By the present invention, there is provided apparatus for pumping a liquid through a chromatographic column filled with an adsorption agent in liquid chromatography, said apparatus comprising an electromagnetic metering pump, having an intake for said liquid and an outlet for said liquid, operable to take in said liquid at said intake and deliver it in a pulsed and pressurized flow at said outlet, connecting means for connecting said outlet with the column and, in said connecting means, a pulsation damping device in the form of a sealed chamber having a resiliently loaded elastic wall.

Metering pumps as used in the present apparatus have been used previously for introducing an exact selected amount of an additive, for example a water softening agent or a coagulating agent, into a stream of water or other liquid. Typically, the metering pump consists of pumping diaphragm and an electromagnet with a central armature fitted with a return spring. The electromagnet is energised by electrical impulses, and on each impulse the pumping diaphragm is moved to and fro. The rate of pumping the additive is controlled by adjusting the stroke of the armature and/or the impulse frequency. The use of such a pump in accordance with the present invention leads to the apparatus being relatively inexpensive. With the apparatus, low pressure chromatography can be carried out more quickly than when the liquid is supplied to the column hydrostatically, and yet still economically.

With the apparatus, a satisfactory chromatographic separation of the different components of the mixture being processed is obtained. Used by itself, the metering pump yields a completely unsatisfactory chromatographic spectrum but it is found that, simple as it is, the said pulsation damping device is effective to give good chromatographic separation of the constituents of the mixture being processed.

The ingress of air to the chamber is found to have an undesirable influence and should not be permitted.

To provide wide versatility in operation, the apparatus may be provided with an adjustable power supply for actuating the metering pump, for example an electric impulse generator of variable impulse frequency. In this way an adjustment of power, even a very exact adjustment of power, can be obtained for the particular conditions. For example, one can, in order to get the optimum speed of operation, adjust the power depending on the amount of the material involved, the viscosity of the liquid and similar factors.

The spring loading of the elastic wall is preferably adjustable so that the pressure in the chamber can be adjusted as required. Satisfactory results are maintained.

A very simple construction enabling the load pressure to be adjusted and changes in the rate of delivery to be reduced to a negligible value is obtained if the elastic wall is loaded by means of a mechanical spring, conveniently a coil spring. Alternatively, or additionally, a gas under pressure may be used to give very fine adjustment both up and down.

Advantageously the sealed chamber is provided with a valve adapted to maintain the pressure in the chamber above a selected minimum value. When, on account of the smallness of the quantity of the liquid, and/or the low value of its viscosity, the pumping pressure cannot be maintained at a value in excess of this minimum pressure, the non-return valve ensures that sufficient pressure to distend the pliable wall of the chamber is maintained.

In a preferred form of the apparatus, a pressure gauge connected with the chamber, is provided to measure the pressure in the chamber. Advantageously closable venting means is provided beyond the gauge so that the chamber may be vented to atmosphere via the gauge. The pressure gauge permits a very simple control and selection of the pressure in the chamber. If air gets into the pressure gauge branch after venting to atmosphere, then the branch can be rinsed through with liquid from the chamber.

Preferably the metering pump has a pumping diaphragm which is moved in one direction by the armature of an electromagnet and returned by a spring. This leads to an especially cheap and robust construction of metering pump. Ideally the stroke of the armature is limited by an adjustable stop. By choice of stroke and/or impulse frequency the pump can be set to suit the particular circumstances.

The metering pump and pulsation damping apparatus may be mounted in a common housing with the connections between the two contained within the housing. This arrangement gives a ready made unit merely requiring the connection of a reservoir.

The invention further provides a process for separating the constituent materials of a mixture using a chromatographic column and an eluent liquid which comprises pumping the eluent liquid by an electromagnetic metering pumping means to form a pulsed flow of said eluent, passing the pulsed flow of eluent via a chamber to an outlet, exposing the eluent whilst in the chamber to a resiliently loaded elastic wall, withdrawing a substantially damped flow of eluent from the chamber, passing said withdrawn flow into one end of the column and thence through said column to provide a stream of eluent through the column and continuing to provide said stream through the column until the materials of said mixture are substantially separated from one another in the direction of said stream.

The outer surface of the said elastic wall is preferably in communication with the atmosphere.

Figure 2:
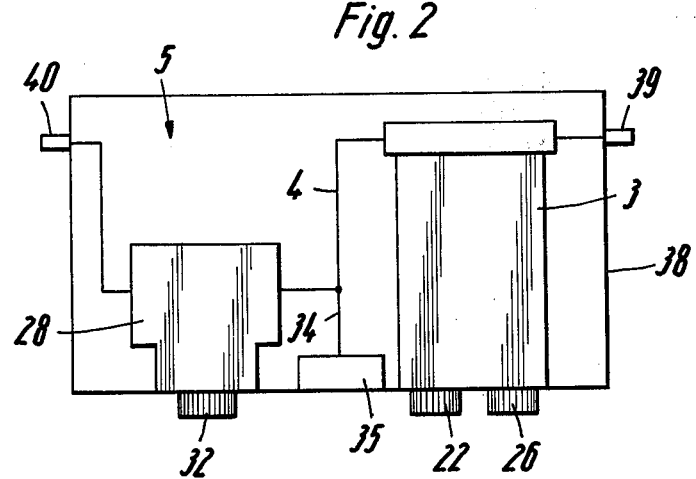

The following description of preferred embodiments of the invention, in which reference is made to the accompanying drawing, is given in order to illustrate the invention. In the drawing:

FIG. 1 shows a first embodiment of the apparatus partly in section and partly schematically, and FIG. 2 shows a second embodiment of the apparatus having a single housing.

In the embodiment of FIG. 1, liquid from a reservoir 1 is drawn up a suction tube 2 by means of an electromagnetic pump 3 and fed via a connecting tube to a pulsation damping unit 5. The liquid passes from the unit 5 via an output tube 6, which is partly a capillary tube, to a two-way valve 7. Valve 7 can be operated to feed the liquid to a chromatographic column 8, filled with an adsorption agent, and thence to a receiver 9, or to feed the liquid to a vent-pipe 10, for example, to allow air to escape from the column.

The electromagnetic pump 3 has a pumping head 11 provided with a suction valve 12 and a delivery valve 13 communicating with a pumping chamber 14. The pumping chamber is bounded on one side by a diaphragm 15 operated by the central armature 16 of an electromagnet 17. On the armature 16 is a shrink fitted plunger element 19. Between a flange 20 on this plunger element and the pump housing is a spring washer 21 which serves as a return spring. The rear face of the central armature is pulled back on to an adjusting screw 22 by this spring. Rotation of screw 22 by an integral adjusting knob moves it forward or backward relative to the casing 23 of the pump. In the bottom 24 of the housing is mounted an electronic control unit 25 which produces a series of exitation impulses for the electromagnet 17. The impulse frequency is adjustable by a control knob 26.

The pulsation damping unit 5 has a housing 27 in which is mounted a pulsation damping device 28 having a chamber 29 bounded on one side by a flexible wall 30 in the form of a diaphragm. The diaphragm is biased by a mechanical spring 31 equipped with an adjusting screw 32. The exit from the expansion chamber is provided with a non-return valve 33, the spring of which is so arranged that it only becomes fully open when the pressure exceeds a selected value. At other times it acts as a throttle to maintain a certain minimum pressure in the expansion chamber. From the expansion chamber a tube 34 leads to a pressure gauge 35 with a dial and a pointer 36. Tube 34 communicates via the gauge 35 with a vent to atmosphere 37. The gauge 35 and tube 34 can be purged by opening vent 37.

To use the apparatus, the reservoir 1 is filled with the requisite liquid. If the pump is then started it propels this liquid through the pulsation damping unit to the column 8. The adsorption agent in the column separates the constituent parts of the material into separate and distinct zones. The rate of flow can be increased, if required, by turning the adjusting knob of screw 22 to increase the stroke and/or by turning the control knob 26 to increase the impulse frequency. The back pressure caused by the resistance of the column 8 depends on such factors as the selected speed and the viscosity of the solvent. To obtain optimum conditions the pressure of the spring 31 is varied by the adjusting screw 32. It has been found suitable in practice if the pressure of the pulsation damping device can be set at values between 0.5 to 3 bars. Within this range it is possible to carry out almost all tests in low pressure chromatography. Should the back pressure fall below 0.5 bars the valve 33 does not open fully so that the pressure in the expansion chamber remains above 0.5 due to the resultant throttling. If the back pressure in the column rises above 3 bars the flow of liquid can be reduced by a suitable throttle valve or by reducing the pump output.

In the embodiment of FIG. 2 the pump 3, the unit 28, the gauge 35, the interconnecting pipework 4 and the branch pipe 34 are contained in a common housing 38. The only external connections are a suction inlet pipe 39 and a delivery pipe 40 for connection respectively to a reservoir such as reservoir 1 and a chromatographic column.

The apparatus as described with reference to the drawings has been tested by using it in the chromatographic separation of various mixtures using a column filled with kieselguhr. Examples of such mixtures are given below with the eluent indicated in brackets.

i. testosterone and hydrocortisone together with other steroids (mixture of chloroform and methanol)
ii. vitamin $D_3$, nicotinamide and nicotinic acid (ethanol)
iii. the insecticides $o_1$ p - DDT and p p - DDT (n - hexane)
iv. the methyl, ethyl and butyl di-esters of a phthalic acid (heptane)

In all of these examples, a satisfactorily sharp separation of the mixture into its constituents was obtained. The effect is shown diagrammatically by zones $a$, $b$ and $c$ in FIG. 1.

It will be understood that the specific embodiments of apparatus described herein with reference to the drawings are given by way of illustration only and that various departures may be made therefrom all within the ambit of the invention. The specific mixtures of substances are cited merely to illustrate the efficacy of the apparatus and method and the results to be expected from the use thereof in practice.

We claim:
1. Apparatus for pumping a liquid through a chromatographic column filled with an adsorption agent in liquid chromatography, said apparatus comprising an electromagnetic metering pump, having an intake for said liquid and an outlet for said liquid, operable to take in said liquid at said intake and deliver it in a pulsed and pressurized flow at said outlet, connecting means for connecting said outlet with the column and, in said connecting means, a pulsation damping device in the form of a sealed chamber having an elastic wall, and adjustable resilient means loading said wall.

2. Apparatus according to claim 1 in which the elastic wall is spring loaded by a coil spring.

3. Apparatus according to claim 1 in which the sealed chamber has an outlet connected to said column which is provided with a valve adapted to maintain the pressure in the chamber above a selected minimum.

4. Apparatus according to claim 1 in which the metering pump has a pumping diaphragm, an armature in operative association with an electromagnet for moving the diaphragm in one direction and a return spring for returning the diaphragm in the opposite direction.

5. Apparatus according to claim 4 having an adjustable stop for adjustably limiting movement of the armature.

6. Apparatus according to claim 1 having a common housing in which are located the metering pump, the pulsation damping device and the connecting means.

7. Apparatus according to claim 1 in which said connecting means includes a capillary tube between said chamber and said column.

8. Apparatus according to claim 1 in association with a chromatographic column connectable with the pulsation damping device.

9. Apparatus for pumping a liquid through a chromatographic column filled with an adsorption agent in liquid chromatography, said apparatus comprising an electromagnetic metering pump, having an intake for said liquid and an outlet for said liquid, operable to take in said liquid at said outlet, connecting means for connecting said outlet with the column, a pulsation damping device in said connecting means in the form of a sealed chamber having an adjustably spring loaded elastic wall, a pressure gauge connected with said chamber and, beyond the pressure gauge closable venting means by which the chamber may be vented to atmosphere via the pressure gauge.

10. Apparatus for pumping a liquid through a chromatographic column filled with an adsorption agent in liquid chromatography, said apparatus comprising an electromagnetic metering pump, having an intake for said liquid and an outlet for said liquid, operable to take in said liquid at said intake and deliver it in a pulsed and pressurized flow at said outlet, connecting means for connecting said outlet with the column, a pulsation damping device in the form of a sealed chamber having a spring loaded elastic wall, a valve adapted to maintain the pressure in the chamber at a selected minimum and an electrical impulse generator of variable impulse frequency for adjustably actuating the electromagnetic metering pump.

11. A process for separating the constituent materials of a mixture using a chromatographic column and an eluent liquid which comprises pumping an eluent liquid by electromagnetic metering pumping means to form a pulsed flow of said eluent, passing the pulsed flow of eluent via a chamber to an outlet, exposing the eluent whilst in the chamber to a resiliently loaded elastic wall, withdrawing a substantially damped flow of eluent from the chamber, passing said withdrawn flow into one end of the column and thence through said column to provide a stream of eluent through the column and continuing to provide said stream through the column until the materials of said mixture are substantially separated from one another in the direction of said stream.

* * * * *